United States Patent
Perschbacher et al.

(10) Patent No.: US 10,765,379 B2
(45) Date of Patent: Sep. 8, 2020

(54) SYSTEMS AND METHODS FOR MEDICAL ALERT MANAGEMENT

(71) Applicant: Cardiac Pacemakers, Inc., St. Paul, MN (US)

(72) Inventors: David L. Perschbacher, Coon Rapids, MN (US); Sunipa Saha, Shoreview, MN (US); JoAnna Trapp Simpson, Eagan, MN (US); Keith Mattson, Lino Lakes, MN (US)

(73) Assignee: Cardiac Pacemakers, Inc., St. Paul, MN (US)

(\*) Notice: Subject to any disclaimer, the term of this patent is extended or adjusted under 35 U.S.C. 154(b) by 24 days.

(21) Appl. No.: 15/967,772

(22) Filed: May 1, 2018

(65) Prior Publication Data

US 2018/0310892 A1 Nov. 1, 2018

Related U.S. Application Data

(60) Provisional application No. 62/492,449, filed on May 1, 2017.

(51) Int. Cl.
*A61B 5/00* (2006.01)
*G16H 50/30* (2018.01)
(Continued)

(52) U.S. Cl.
CPC .............. *A61B 5/746* (2013.01); *A61B 5/002* (2013.01); *A61B 5/0452* (2013.01);
(Continued)

(58) Field of Classification Search
CPC ....... A61B 5/746; A61B 5/7275; A61B 5/002; A61B 5/7282; A61B 5/0452;
(Continued)

(56) References Cited

U.S. PATENT DOCUMENTS 8,781,847 B2 7/2014 Simms et al.
9,259,177 B2 2/2016 Drew et al.
(Continued)

FOREIGN PATENT DOCUMENTS

WO WO-2018204307 A1 11/2018

OTHER PUBLICATIONS

Hoyme, Kenneth P., et al., "System and Method for Managing Coordination of Collected Patient Data in an Automated Patient Management System, U.S. Appl. No. 11/121,593, filed May 3, 2005".

(Continued)

*Primary Examiner* — Brian Wilson
(74) *Attorney, Agent, or Firm* — Schwegman Lundberg & Woessner, P.A.

(57) ABSTRACT

Systems and methods for managing machine-generated medical alerts associated with physiological events detected from one or more patients are described herein. An alert management system may receive medical events detected from a patient and physiological data associated with patient historical medical alerts. The system comprises an alert prioritizer circuit to generate an event priority indicator for the detected medical event, using a comparison between the detected medical event and the physiological data associated with patient historical medical alerts. The system can identify prolific alert patients using the information about the historical medical alerts. The alert prioritizer circuit can adjust a priority of the detected medical event, and an output circuit can present a priority to a user or a process using the event priority indicator and the identification of prolific alert patient.

20 Claims, 7 Drawing Sheets

(51) Int. Cl.
  *A61B 5/053* (2006.01)
  *A61B 5/0452* (2006.01)
  *A61N 1/372* (2006.01)
  *G16H 40/67* (2018.01)
  *A61N 1/36* (2006.01)
  *G16H 40/20* (2018.01)

(52) U.S. Cl.
  CPC ............ *A61B 5/0535* (2013.01); *A61B 5/686* (2013.01); *A61B 5/7275* (2013.01); *A61B 5/7282* (2013.01); *A61N 1/36135* (2013.01); *A61N 1/37258* (2013.01); *G16H 40/20* (2018.01); *G16H 40/67* (2018.01); *G16H 50/30* (2018.01); *A61B 5/6869* (2013.01)

(58) Field of Classification Search
  CPC ..... A61B 5/0535; A61B 5/686; A61B 5/6869; A61N 1/36135; A61N 1/37258; G16H 40/20; G16H 40/67; G16H 50/30
  See application file for complete search history.

(56) References Cited

U.S. PATENT DOCUMENTS

| | | | |
|---|---|---|---|
| 2004/0122296 A1* | 6/2004 | Hatlestad | A61B 5/02055 600/300 |
| 2005/0060186 A1 | 3/2005 | Blowers et al. | |
| 2005/0242928 A1 | 11/2005 | Kirkeby | |
| 2006/0047538 A1 | 3/2006 | Condurso et al. | |
| 2006/0206011 A1* | 9/2006 | Higgins | A61B 5/002 600/300 |
| 2006/0253300 A1 | 11/2006 | Somberg et al. | |
| 2009/0054735 A1 | 2/2009 | Higgins et al. | |
| 2012/0226108 A1* | 9/2012 | Osorio | G16H 50/20 600/301 |
| 2013/0197944 A1 | 8/2013 | Drew et al. | |

OTHER PUBLICATIONS

Mahajan, Deepa, et al., "Physiologic Event Detection and Data Storage, U.S. Appl. No. 62/109,963, filed Jan. 30, 2015".

Perschbacher, David L., et al., "Atrial Fibrillation Detection, U.S. Appl. No. 62/142,184, filed Apr. 2, 2015".

Somberg, Benjamin L., et al., "System and Method for Managing Patient Triage in an Automated Patient Management System, U.S. Appl. No. 11/121,594, filed May 3, 2005".

"International Application Serial No. PCT/US2018/030361, International Search Report dated Jul. 4, 2018", 4 pgs.

"International Application Serial No. PCT/US2018/030361, Written Opinion dated Jul. 4, 2018", 5 pgs.

* cited by examiner

SYSTEMS AND METHODS FOR MEDICAL ALERT MANAGEMENT

CLAIM OF PRIORITY

This application claims the benefit of priority under 35 U.S.C. § 119(e) of U.S. Provisional Patent Application Ser. No. 62/492,449, filed on May 1, 2017, which is herein incorporated by reference in its entirety.

TECHNICAL FIELD

This document relates generally to automated patient management, and more particularly, to systems, devices and methods for managing alert notifications in an automated patient management system.

BACKGROUND

Implantable medical devices (IMDs) have been used for monitoring patient health condition or disease states and delivering therapies. For example, implantable cardioverter-defibrillators (ICDs) are used to monitor certain abnormal heart rhythms. Some IMDs may be used to monitor progression of a chronic disease, such as worsening of cardiac performance due to congestive heart failure (CHF). In addition to diagnostic capabilities, the IDs may also provide therapies to treat or alleviate certain medical conditions, such as cardiac electrostimulation therapies to treat cardiac arrhythmias or to rectify cardiac dyssynchrony in CHF patients.

The IMDs may generate alert notification when the occurrence of an alert condition triggers a notification scheme. The alert condition may include a detection of a particular health condition or a medical event, such as a cardiac arrhythmia or worsening heart failure. The alert notification may be provided to a healthcare provider to signal the patient health condition. Upon being notified, the healthcare provider may review patient medical record or device recorded physiological data, determine the presence or causes of the medical event, or assess whether a prescribed therapy has resulted in desired therapeutic outcome.

A patient management system may monitor patients with IMDs that are interconnected to the patient management via a data communications network, such as the Internet. Such a patient management system have enabled healthcare providers to remotely follow up with the patients or to assess device functions on a periodic basis.

OVERVIEW

A patient management system may manage a large volume of alert notifications corresponding to physiological events detected from ambulatory medical devices (AMDs). For example, in managing a cohort of AMD patients in a clinic, the patient management system may frequently receive alert notifications on various cardiac arrhythmia episodes or worsening heart failure (WHF) events detected by the implantable cardiac devices, such as a cardiac monitor, a pacemaker, an implantable defibrillator, or a cardiac resynchronization therapy device. The implantable cardiac devices may sense physiological data associated with the alerts, and store the physiological data in the implantable cardiac devices. The implantable cardiac devices may be interrogated, and the physiological data may be retrieved and transmitted to the patient management system. A clinician may review the alerts and the physiological data, and take further actions such as adjudicate the device-detected cardiac arrhythmia episodes, schedule patient follow-up visits, or reprogram the implantable cardiac devices.

With a large number of AMDs connected to the patient management system, reviewing the alerts from all the patients requires significant amount of time and resources, and can be costly or otherwise time consuming for a healthcare facility. The present inventors have recognized a substantial challenge in efficient medical alert management, and particularly a need for an approach to providing automated remote patient management through a configurable evaluation, prioritization, and presentation of alert notifications. Such systems and methods may help increase timely medical attention to patients with alerts associated with critical medical conditions.

This document discusses, among other things, systems, devices, and methods for managing machine-generated medical alerts associated events detected by ambulatory devices such as AMDs. A patient management system may include a detector circuit to detect medical events in a patient. An alert prioritizer circuit may generate an event priority indicator for the detected medical event using a comparison between the detected medical event and information about patient historical medical alerts. The system may additionally include a patient identifier circuit to identify prolific alert patients (PAPs) using the information about the historical medical alerts. An output circuit can be configured to adjust a priority of the detected medical event using the event priority indicator and the identification of PAPs. The output circuit may schedule a presentation of the detected medical event to a user or a process using the adjusted priority.

Example 1 is a system for managing machine-generated medical alerts. The system comprises a receiver circuit configured to receive a medical event detected from a patient and information of historical medical alerts associated with the patient; an alert prioritizer circuit configured to generate an event priority indicator for the detected medical event using the detected medical event and the information of historical medical alerts; and an output circuit configured to output a priority of the detected medical event, such as for presenting the detected medical event to a user or a process, using the event priority indicator.

In Example 2, the subject matter of Example 1 optionally includes the alert prioritizer circuit that may be configured to adjust the priority of the detected medical event by lowering the priority of the detected medical event when the detected medical event is similar to events in the information of historical medical alerts.

In Example 3, the subject matter of any one or more of Examples 1-2 optionally includes the alert prioritizer circuit that may be adjust the priority of the detected medical event by increasing the priority of the detected medical event when the detected medical event is dissimilar to events in the information of historical medical alerts.

In Example 4, the subject matter of any one or more of Examples 1-3 optionally includes the information of the historical medical alerts that may include existing alerts stored in a memory.

In Example 5, the subject matter of any one or more of Examples 1-4 optionally includes a patient identifier circuit configured to identify a prolific alert patient, the prolific alert patient having a quantity of historical medical alerts exceeding a threshold value (e.g., a threshold quantity value) during a specified time period. The output circuit may be configured to adjust the priority of the detected medical event using the identification of the prolific alert patient. The output circuit may be configured to schedule the presentation of the detected medical event using the identification of the prolific alert patient.

In Example 6, the subject matter of any one or more of Examples 1-5 optionally includes a sensor circuit configured to sense a physiological signal from the patient, and a detector circuit configured to detect the medical event using the sensed physiological signal. The alert prioritizer circuit may be configured to generate the event priority indicator using a comparison between the detected medical event and the information of historical medical alerts.

In Example 7, the subject matter of Example 6 optionally includes the information of historical medical alerts that may include a plurality of historical physiological signal characteristics corresponding to the historical medical alerts. The alert prioritizer circuit may be configured to: extract a signal characteristic from the sensed physiological signal in response to the detection of the medical event; compute a similarity metric between (1) the extracted signal characteristic corresponding to the detected medical event and (2) the plurality of the historical physiological signal characteristics corresponding to the historical medical alerts; and generate the event priority indicator using the similarity metric.

In Example 8, the subject matter of Example 7 optionally includes the alert prioritizer circuit that may be configured to: generate a representative historical signal characteristic from the plurality of historical physiological signal characteristics corresponding to the historical medical alerts; and compute a similarity metric between (1) the extracted signal characteristic corresponding to the detected medical event and (2) the representative historical signal characteristic.

In Example 9, the subject matter of Example 7 optionally includes the historical medical alerts that may include one or more alert clusters each comprising a respective plurality of historical physiological signal characteristics. The alert prioritizer circuit may be configured to compute one or more similarity metrics between the extracted signal characteristic corresponding to the detected medical event and the respective plurality of historical physiological signal characteristics of the one or more clusters, and generate the event priority indicator using the one or more similarity metrics and a cluster priority.

In Example 10, the subject matter of Example 9 optionally includes the one or more clusters that may include at least one of: a true positive alert cluster comprising historical physiological signal characteristics corresponding to true positive detections of historical medical events; or a false positive alert cluster comprising historical physiological signal characteristics corresponding to false positive detections of historical medical events.

In Example 11, the subject matter of Example 9 optionally includes the one or more clusters that may include one or more medical event types.

In Example 12, the subject matter of Example 9 optionally includes the one or more clusters that may include one or more value ranges of a physiological parameter.

In Example 13, the subject matter of any one or more of Examples 1-12 optionally includes the output circuit that may be configured to schedule a human-perceptible notification of the detected medical event using the adjusted priority.

In Example 14, the subject matter of Example 13 optionally includes the alert prioritizer circuit that may be configured to generate, for a plurality of detected medical events, respective event priority indicators. The alert prioritizer circuit may be configured to adjust priorities of the plurality of detected medical events using the respective event priority indicators, and schedule a human-perceptible notification including a presentation of the plurality of medical events arranged in a descending order of the adjusted priorities.

In Example 15, the subject matter of any one or more of Examples 1-14 optionally includes a memory circuit that may be further configured to store the information of historical medical alerts, and update the information of historical medical alerts by storing in the memory circuit the detected medical event.

Example 16 is a machine-readable storage medium, comprising a plurality of instructions that, responsive to being executed with processor circuitry of a computing device, cause the computing device to: receive a medical event detected from a patient and information of historical medical alerts associated with the patient; generate an event priority indicator for the detected medical event using the detected medical event and the information of historical medical alerts; and adjust a priority of the detected medical event, such as for presenting the detected medical event to a user or a process, using the event priority indicator.

In Example 17, the subject matter of Example 16 optionally includes an instruction that causes the computing device to identify a prolific alert patient, the prolific alert patient having a quantity of historical medical alerts exceeding a threshold quantity value during a specified time period. The instruction to adjust the priority of the detected medical event includes further using the identification of the prolific alert patient.

In Example 18, the subject matter of Example 16 optionally include the information of historical medical alerts that may include a plurality of historical physiological signal characteristics corresponding to the historical medical alerts. The machine-readable storage medium further comprises instructions that cause the computing device to: receive a physiological signal sensed during the detected medical event; extract a signal characteristic from the received physiological signal; and compute a similarity metric between (1) the extracted signal characteristic corresponding to the detected medical event and (2) the plurality of the historical physiological signal characteristics corresponding to the historical medical alerts; generate the event priority indicator inversely related to the similarity metric.

In Example 19, the subject matter of Example 16 optionally include the instruction to generate the event priority indicator that may include instructions that cause the computing device to: generate a representative historical signal characteristic from the plurality of historical physiological signal characteristics corresponding to the historical medical alerts; and compute a similarity metric between (1) the extracted signal characteristic corresponding to the detected medical event and (2) the representative historical signal characteristic.

Example 20 is a method for managing machine-generated medical alerts via a medical system. The method comprises steps of: receiving a medical event detected from a patient and information of historical medical alerts associated with the patient; generating an event priority indicator for the detected medical event using the detected medical event and the information of historical medical alerts; and adjusting the priority of the detected medical event using the event priority indicator.

In Example 21, the subject matter of Example 20 optionally includes adjusting the priority that may include one or more of lowering the priority of the detected medical event when the detected medical event is similar to events in the information of historical medical alerts, or increasing the priority of the detected medical event when the detected medical event is dissimilar to events in the information of historical medical alerts.

In Example 22, the subject matter of Example 20 optionally includes identifying a prolific alert patient. The prolific alert patient may have a quantity of the historical medical alerts exceeding a threshold quantity value during a specified time period. The scheduling of the presentation of the detected medical event may include further using the identification of the prolific alert patient.

In Example 23, the subject matter of Example 20 optionally includes the information of historical medical alerts that may include a plurality of historical physiological signal characteristics corresponding to the historical medical alerts. The subject matter optimally includes steps of: receiving a physiological signal from the patient during the detected medical event; extracting a signal characteristic from the received physiological signal; computing a similarity metric between (1) the extracted signal characteristic corresponding to the detected medical event and (2) the plurality of the historical physiological signal characteristics corresponding to the historical medical alerts; and generating the event priority indicator inversely related to the similarity metric.

In Example 24, the subject matter of Example 23 optionally includes a step of generating a representative historical signal characteristic from the plurality of historical physiological signal characteristics corresponding to the historical medical alerts. The similarity metric may be computed as a distance between (1) the extracted signal characteristic corresponding to the detected medical event and (2) the representative historical signal characteristic.

In Example 25, the subject matter of Example 23 optionally includes the historical medical alerts that may include one or more alert clusters each comprising a respective plurality of historical physiological signal characteristics. The similarity metric may include one or more similarity metrics between the extracted signal characteristic corresponding to the detected medical event and the respective plurality of historical physiological signal characteristics of the one or more clusters. The event priority indicator may be generated using the one or more similarity metrics and a cluster priority.

The systems, devices, and methods discussed in this document may improve the technology of automated alert management. One of the challenges in medical alert management is that clinicians need to attend to overwhelmingly large amount of alert notifications from patients. The present document provides a technological solution to this technical challenge by exploring and utilizing, among other things, information about intra-patient and inter-patient variations of their alert notifications, thereby helping clinicians prioritize their large amount of alert notifications. In one aspect, the present inventors have recognized that alerts associated with device-detected physiological events from a patient (e.g., cardiac arrhythmias or worsening heart failure events) may represent different degrees of severities. Alerts may be prioritized according to their degrees of severities before being presented to a clinician for evaluation. For example, an AMD patient may have device-detected cardiac arrhythmia events in his/her medical history. The device-detected cardiac arrhythmia events may be designated as true positive (TP) detections or false positive (FP) detections. The TP detections are detected arrhythmia episodes that are truly the target arrhythmia type, and the FP detections are detected arrhythmia episodes that are indeed non-arrhythmic event or belong to other types of arrhythmia different from the target arrhythmia. If a device-detected arrhythmia episode resembles a historical TP detection, then the detected arrhythmia episode is more likely a true target arrhythmia. As such, a higher severity is indicated and a higher priority is designated. However, if the device-detected arrhythmia episode resembles a historical FP detection, then it is less likely a true target arrhythmia event. As such, a lower severity is indicated, and a lower priority is designated. Compared to conventional alert systems that provide to clinicians a large amount of alerts associated with events with mixed severities, the prioritization of device-detected arrhythmia events (such as using the comparison with patient historical TP or FP detections as discussed in this documents), may improve the alert management system's performance in recognizing high-severity physiological events with higher accuracy (i.e., lower false alert rate), and timely alerting clinicians to such events, yet at little to no additional cost or system complexity.

In addition to the variation of severity among the alerts within a patient, alerts from multiple patients may demonstrate inter-patient variation in alert severity. The present inventors have recognized that quantity or frequency of alert notifications presented to a patient management system may have a skewed distribution across the patients being monitored. For example, a majority of alert notifications may come from a small percentage of the patients. These patients, hereinafter referred to as prolific alert patients (PAPs), may have alerts associated with medical events having substantially similar characteristics. Some PAP may have frequent alerts corresponding to patient manually activated events. The alert prioritization discussed in this document may timely direct medical attention to patients likely having more severe events than those likely having frequent false positive detections. This might help better align the medical resources to serve the need of more patients, but may also help save the operational cost in the healthcare facilities. For example, by identifying patients with lower priority alerts (such as PAPs), fewer unnecessary medical interventions, such as drugs, procedures, or device therapies, may be scheduled, prescribed, or provided to such patients. As a result, overall system cost savings may be realized.

The alert notification evaluation and prioritization as discussed in this document may also improve the functionality of a patient management system. The alert prioritization as discussed herein may be configured to evaluate and prioritize events detected by various physiological event detectors or AMDs. The alert prioritization may be implemented in, and executed by, the AMD or an external system such as a communicator, mobile monitor, programmer, or a remote patient management system in communication with patient AMDs. As such, in some cases, improved alert management may be achieved without a modification of existing patient AMDs or physiological event detectors. Additionally, the system memory may be more efficient by storing a smaller number of alerts associated with medical events of higher severity and/or physiological information clinically more relevant to medical diagnosis (e.g., for diagnosing types of arrhythmias patient has suffered from).

The discussion of alert prioritization in this document focuses on alerts of cardiac arrhythmias detected by AMDs. However, this is meant only by way of example and not limitation. It is within the contemplation of the inventors, and within the scope of this document, that the systems, devices, and methods discussed herein may also be used to evaluate and prioritize patient alerts of other medical conditions, such as detection of worsening of chronic conditions such as heart failure, respiratory disease, or renal dysfunctions, among others. Additionally, although systems and methods are described as being operated or exercised by clinicians, the entire discussion herein applies equally to organizations, including hospitals, clinics, and laboratories, and other individuals or interests, such as researchers, scientists, universities, and governmental agencies, seeking access to the patient data.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for managing machine-generated medical alerts associated with physiological events detected from one or more patients. A patient management system may receive medical events detected from a patient, and generate an event priority indicator for the detected medical event using a comparison between the detected medical event and historical medical alerts. The system may additionally identify prolific alert patients (PAPs) using the information about the historical medical alerts. The system may adjust a priority of the detected medical event for presenting the event to a user or a process using the event priority indicator and the identification of the PAPs.

Figure 1:
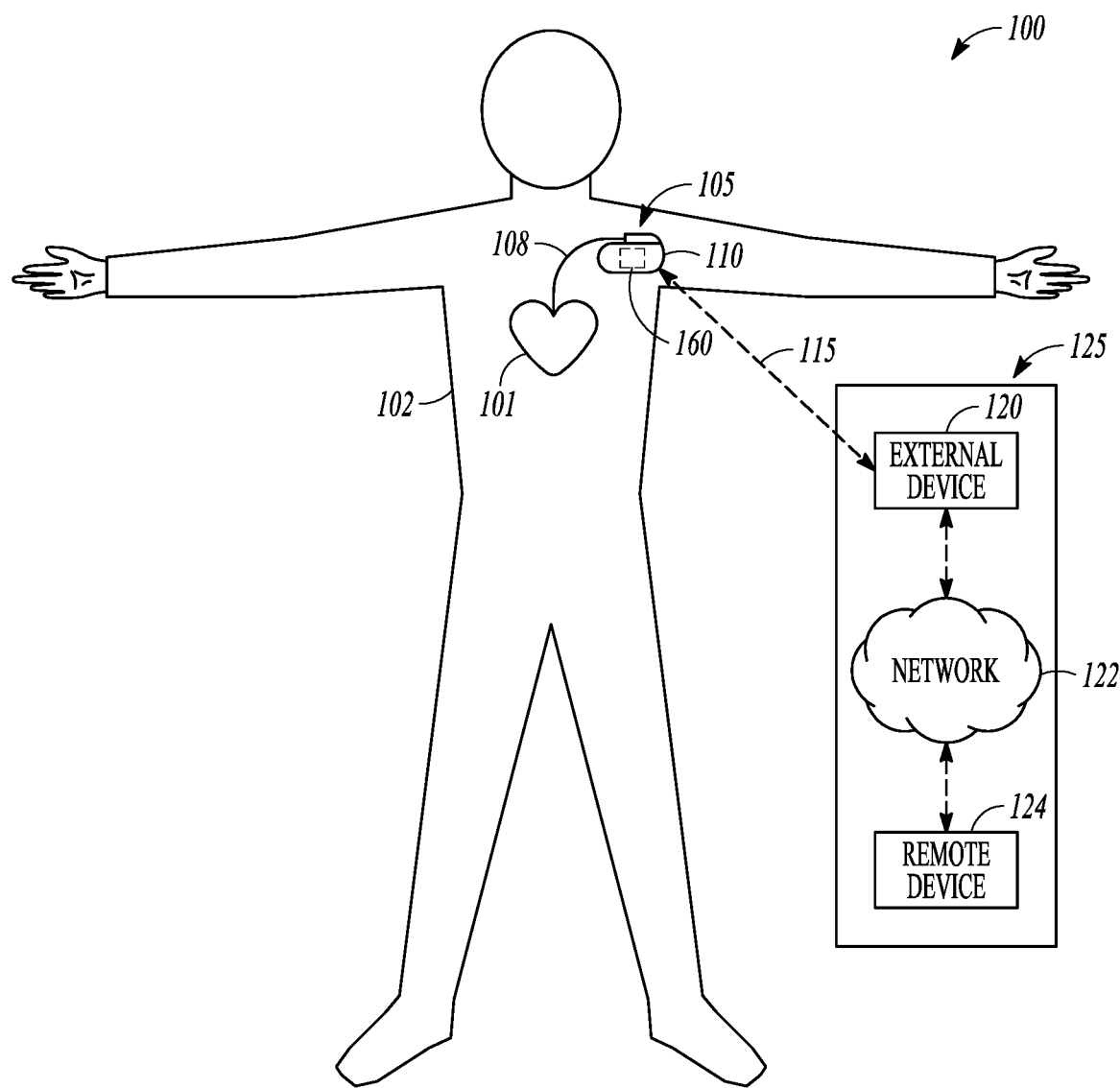
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be configured to be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the ambulatory system 105 may include one or more leadless sensors not being tethered to the AMD 110 via the lead system 108. The leadless ambulatory sensors may be configured to sense a physiological signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature.

In an example, the AMD 110 may include a detector circuit 160 for detecting a medical event from the sensed physiological signals. In an example, the medical event includes a specific cardiac arrhythmia. Examples of cardiac arrhythmias may include atrial or ventricular brady- or tachy-arrhythmia, such as atrial fibrillation, atrial flutter, atrial tachycardia, supraventricular tachycardia, ventricular tachycardia, or ventricular fibrillation, among others. In an example, the cardiac arrhythmia detection circuit 160 is configured to detect worsening of a chronic medical condition, such as heart failure. In another example, the medical event may include patient-triggered events.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmias, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmias or complications from arrhythmias.

The external system 125 may include a dedicated hardware/software system such as a programmer, a remote server-based patient management system, or alternatively a system defined predominantly by software running on a standard personal computer. The external system 125 may manage the patient 102 through the AMID 110 connected to the external system 125 via a communication link 115. This may include, for example, programming the AMD 110 to perform one or more of acquiring physiological data, performing at least one self-diagnostic test (such as for a device operational status), analyzing the physiological data to detect a cardiac arrhythmias, or optionally delivering or adjusting a therapy to the patient 102. Additionally, the external system 125 may receive device data from the AMD 110 via the communication link 115. Examples of the device data received by the external system 125 may include real-time or stored physiological data from the patient 102, diagnostic data such as detection of cardiac arrhythmias or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMID 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. In some examples, the alert conditions may alternatively or additionally be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible. The server may include an alert prioritizer circuit configured to prioritize the alert notifications. For example, an alert of a detected medical event may be prioritized using a similarity metric between the physiological data associated with the detected medical event to physiological data associated with the historical alerts. Examples of the alert analyzer and prioritizer circuits are discussed below, such as with reference to FIGS. 4-5.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. Example systems are described in commonly-assigned U.S. patent application, entitled, "System and Method for Managing Coordination of Assembled Patient Data in an Automated Patient Management System," Ser. No. 11/121,593, filed May 3, 2005, and U.S. patent application, entitled, "System and Method for Managing Patient Triage in an Automated Patient Management System," Ser. No. 11/121,594, filed May 3, 2005, the disclosures of which are incorporated by reference. In addition to generating alert notifications, the remote device 124, including the server and the interconnected clients, may also execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a system user such as the patient or a clinician, or to a process including, for example, an instance of a computer program executable in a microprocessor. In an example, the process may include an automated generation of recommendations for anti-arrhythmic therapy, or a recommendation for further diagnostic test or treatment. In an example, the external device 120 or the remote device 124 may include a respective display unit for displaying the physiological or functional signals, or alerts, alarms, emergency calls, or other forms of warnings to signal the detection of arrhythmias. In some examples, the external system 125 may include an external data processor configured to analyze the physiological or functional signals received by the AMD 110, and to confirm or reject the detection of arrhythmias. Computationally intensive algorithms, such as machine-learning algorithms, may be implemented in the external data processor to process the data retrospectively to detect cardia arrhythmias.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
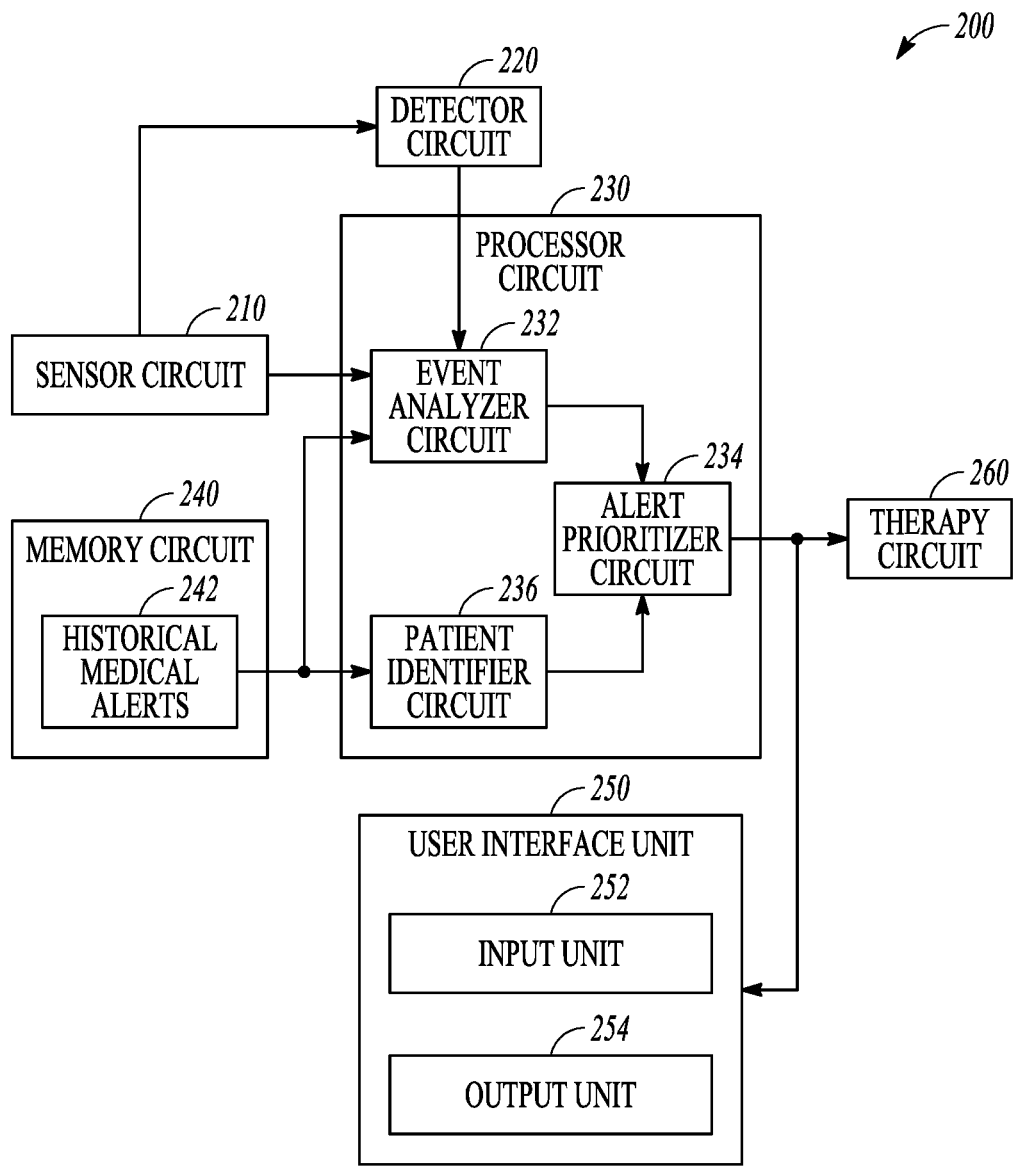
FIG. 2 illustrates generally an example of an alert management system configured to evaluate and prioritize alerts of medical events associated with one or more patients.

FIG. 2 illustrates generally an example of an alert management system 200 that may be configured to evaluate and prioritize alerts of medical events associated with one or more patients. At least a portion of the alert management system 200 may be implemented in the AMD 110, the external system 125 such as one or more of the external device 120 or the remote device 124, or distributed between the AMD 110 and the external system 125. As illustrated in FIG. 2, the alert management system 200 may include one or more of a sensor circuit 210, a detector circuit 220, a processor circuit 230, and a user interface unit 250. The alert management system 200 may additionally be configured as a therapeutic system that includes an optional therapy circuit 260 for delivering a therapy to treat a disease or to alleviate a medical condition.

The sensor circuit 210 may include a sense amplifier circuit to sense a physiological signal sensed from a patient via one or more implantable, wearable, or otherwise ambulatory sensors or electrodes associated with the patient. The sensors may be incorporated into, or otherwise associated with an ambulatory device such as the AMD 110. Examples of the physiological signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more sub-circuits to digitize, filter, or perform other signal conditioning operations on the received physiological signal.

The detector circuit 220 may be coupled to the sensor circuit 210 to detect a target medical event from the sensed physiological signals. In some examples, the physiological signals sensed from a patient may be stored in a storage device, such as an electronic medical record (EMR) system. The detector circuit 220 may be configured to receive a physiological signal from the storage device in response to a user input or triggered by a specific event, and detect a target medical event from the received physiological signals. In an example, the target medical event may include a cardiac arrhythmia episode. The detector circuit 220 may detect the cardiac arrhythmia using heart rates, heart rate statistics such as heart rate stability or variability, atrioventricular activation patterns (e.g., timing relationship between atrial activation and ventricular activation within a cardiac cycle), morphologies of cardiac electrical or mechanical signals, or hemodynamic parameters. In an example, the detector circuit 220 may be configured to detect atrial fibrillation (AF) using a heart rate density index (HRDI) representing a percentage of the heart beats falling within the histogram bin including the mode of the heart rates, such as those disclosed in the commonly assigned Mahajan et al. U.S. Provisional Patent Application Ser. No. 62/142,184, entitled "ATRIAL FIBRILLATION DETECTION," filed Apr. 2, 2015, which is hereby incorporated by reference in its entirety, including its disclosure of the HRDI and the AF detection using at least the HRDI. In another example, the detector circuit 220 may be configured to detect AF using characterization of heart beat as stable beats, unstable beats, or random beats, such as those disclosed in the commonly assigned Mahajan et al. U.S. Provisional Patent Application Ser. No. 62/109,963, entitled "PHYSIOLOGIC EVENT DETECTION AND DATA STORAGE," filed on Jan. 30, 2015, which is hereby incorporated by reference in its entirety, including its disclosure of beats classes and AF detection using at least the beat classes. In another example, the target medical event may include worsening chronic medical condition, such as worsening heart failure (WHF). The detector circuit 220 may detect the WHF by detecting a trend of a physiological signal metric, such as one or more of a decrease in thoracic impedance, an increase in respiration rate or a rapid-shallow breathing index (RSBI) computed as a ratio of a respiratory rate measurement to a tidal volume measurement, an increase in intensity or timing of a heart sound component, among others. In some examples, the detector circuit 220 may detect patient-triggered events. This may include, for example, a button push or other actuator means on the AMD 110, a handheld device, or through the user interface 250 when the patient experiences a symptom of an onset, or a precursor, of the target medical event.

In some examples, the detector circuit 220 may receive contextual data such as time of day, temperature, or other environmental parameters, in addition to the physiological data sensed from the patient. The detector circuit 220 may also receive user input, such as patient medical information (e.g., answers to health questions) entered by the patient or a healthcare provider such as via a user interface unit 250. The detector circuit 220 may use the sensed physiological signals, optionally along with the contextual or environmental information or user input data, to detect the target medical event.

The processor circuit 230, coupled to the detector circuit 220 and the sensor circuit 210, may be configured to generate an event priority indicator for the detected medical event. The processor circuit 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

The processor circuit 230 may include circuit sets comprising one or more other circuits or sub-circuits, such as an event analyzer circuit 232, an alert prioritizer circuit 234, and an optional patient identifier circuit 236. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The event analyzer circuit 232 may be coupled to the sensor circuit 210 and the detector circuit 220. In response to the detection of the target medical event by the detector circuit 220, the event analyzer circuit 232 may receive from the sensor circuit 210 the physiological data used for detecting the target medical event. The event analyzer circuit 232 may also be coupled to a memory circuit 240 that stores and maintains a database containing information about patient historical medical alerts 242. The information about the historical medical alerts 242 may include physiological data associated with existing medical alerts or medical alerts in the patient medical history. The physiological data in the database may be of the same type as the physiological data associated with the detected medical event. For example, if the detector circuit 220 detects a target cardiac arrhythmia (e.g., AF) using a cardiac electrogram sensed according to a specific sensing vector that include one or more electrodes from the lead system 108, then the stored physiological data corresponding to the historical medical alerts 242 may also include cardiac electrograms sensed according to the same sensing vector.

The event analyzer circuit 232 may evaluate the detected medical event against the stored information about the historical medical alerts 242. In some examples, the system 200 may include a receiver circuit in lieu of the sensor circuit 210 and the detector circuit 220. The receiver circuit may be configured to receive a medical event detected from a patient and information of historical medical alerts associated with the patient. The event analyzer circuit 232 may be coupled to the receiver circuit to evaluate the detected medical event against the stored information about the historical medical alerts 242. In an example, in response to the detection of the target medical event, the event analyzer circuit 232 may compare the physiological data associated with the detected medical event against the stored physiological data associated with the historical medical alerts 242. In an example, a similarity metric may be computed between the physiological data associated with the detected medical event and the stored physiological data associated with the historical medical alerts. Examples of the alert evaluation and similarity computation are discussed below, such as with reference to FIGS. 3A-B.

The alert prioritizer circuit 234 may generate an event priority indicator for the detected medical event using the similarity metric between the physiological data associated with the detected medical event and the stored physiological data associated with the historical medical alerts. The alert prioritizer circuit 234 may include a comparator circuit that compares the similarity metric to one or more threshold values, or ranges of values, to categorize the detected medical event into one of a plurality of predetermined degrees of priority, such as a high priority, medium priority, or low priority. In an example, the categorization may be such that the degree of priority is inversely related to the similarity metric, such that a lower priority may be assigned to a detected medical event that is more similar to the historical alerts, and a higher priority may be assigned to a detected medical event that is less similar to the historical alerts. The present inventors have recognized that a detected medical event that is dissimilar to the historical alerts may represent a medical condition not seen in patient medical history, or a substantial variation or progression of a historical medical event that may require immediate medical attention. Assigning a higher priority to such medical events with unprecedented characteristics may alert the healthcare provider to timely review the detected event, evaluate the patient status, or provide prompt intervention or therapy accordingly. Additionally, such an event prioritization may facilitate timely integration of the newly detected medical event, optionally along with user adjudication and annotation, into the database of historical medical alerts 242, as to be discussed below.

In some examples, the information about the historical medical alerts 242 may include indicators of severity or clinical significance of the medical events associated with the historical medical alerts. The severity indicators may be provided by a clinician. In an example, historical medical events that result in physician intervention or hospitalization may be designated as severe historical medical alerts. The alert prioritizer circuit 234 may compare the detected medical event to the severe historical medical alerts and to other non-severe historical medical alerts (such as annotated by a clinician, or those alerts not resulting in hospitalization or intervention). The alert prioritizer circuit 234 may assign a higher priority to a detected medical event that is similar to the severe historical medical alert, or dissimilar to the severe or non-severe historical alerts, and assign a lower priority to a detected medical event that is similar to the non-severe historical alerts. The medical events with characteristics similar to severe medical events in patient medical history are likely of clinical significance. Assigning a higher priority to such events may ensure immediate medical attention and intervention as needed. In some examples, the alert prioritizer circuit 234 may assign a highest priority to the detected medical event that is similar to the severe historical alert, followed by the detected medical event dissimilar to the severe or non-severe historical alerts, and assign a lowest priority to the detected medical event that is similar to the non-severe historical alerts.

The processor circuit 230 may include an optional patient identifier circuit 236 coupled to the memory circuit 240. The patient identifier circuit 236 may be configured to identify, from a plurality of patients, at least one prolific alert patient (PAP) using the stored information about the patient historical medical alerts 242. A PAP is one having a large quantity of medical alerts of the same type (e.g., alerts of atrial fibrillation episodes) within a specific time period. The present inventors have recognized that among the alert notifications presented to a patient management system, a majority of the alert notifications may come from a small percentage of the PAPs. Frequent alerts may reflect patient underlying medical conditions. For example, some PAPs may experience frequent recurrence of the same type of medical condition, such as ventricular arrhythmia storm, post-operative (e.g., cardioversion) recurrent atrial fibrillation, or stress-related instability of medical conditions. Frequent alerts may also be caused by the event detection and alert reporting system. For example, an arrhythmia detection system may repetitively produce false positive detections of an arrhythmia in a patient. In some patients, a detection system may intermittently detect an underlying sustained medical condition in a patient, resulting in multiple separated alerts each having a relative short duration, also known as fractured alerts. In an example of WHF detection, fracture alerts may be caused by repeated detections and loss of detections of a single underlying WHF event, and are more likely to happen when the patient's response to the underlying WHF event fluctuates. Frequent alerts may also include patient-triggered events. As previously discussed, alerts may be activated by a patient, such by pushing a button on an implantable or otherwise ambulatory device, or a handheld device, when the patient experiences an onset of a medical event. It has been noticed that some PAPs are more prone to frequent activations of the triggers such as due to elevated anxiety, which results in frequent and large volume of alert notifications.

The patient identifier circuit 236 may designate a patient as a PAP if a total count of historical medical alerts 242 of the patient exceeds a threshold, or if a frequency of historical medical alerts 242, computed as the quantity of historical medical alerts within a specific period of time (e.g., a week or a month), exceeds a threshold value. Frequent alerts from a PAP may likely be repeating alerts associated with medical events of substantially similar characteristics, repeating false positive detections, or frequent patient-triggered events. As such, in prioritizing the alerts such as for evaluation and adjudication by a healthcare provider, the large volume of alerts from a PAP may be of less significance than the alerts from non-PAP. The patient identifier circuit 236 may assign a lower subject priority to the identified PAP, and assign a high subject priority to the non-PAP.

In an example, the system 200 may monitor, evaluate, and prioritize medical events from multiple patients in a clinic who have their AMDs interconnected to the system 200. Each of these patients may have one or more detected medical events. The alert prioritizer circuit 234 may prioritize the medical events of the multiple patients using both the similarity metrics between the detected medical event and the historical medical alert provided by the event analyzer circuit 232, and the identification of the PAP provided by the patient identifier circuit 236. In an example, the prioritization may include a subject prioritization and an event prioritization. The subject prioritization may include identification of at least a PAP and assignment of a lower subject priority thereto. Within each patient or each PAP, the event prioritization may be using the similarity metric between the detected medical event and the historical medical alerts, such that a lower event priority is assigned to a medical event that is more similar to the historical medical alerts, and a higher event priority is assigned to a medical event that is less similar to the historical medical alerts.

The user interface unit 250 may include an input unit 252 and an output unit 254. In an example, at least a portion of the user interface unit 250 may be implemented in the external system 125. The input unit 252 may receive user input for programming the detector circuit 220, such as parameters and threshold values for detecting a cardiac arrhythmia, or a WHF event, among others. The input unit 252 may include an input device such as a keyboard, on-screen keyboard, mouse, trackball, touchpad, touchscreen, or other pointing or navigating devices. The input unit 252 may receive user input, via the input device, for programming the processor circuit 230, such as parameters and threshold values for computing similarity metric between the detected medial event and the historical medical alerts, identifying PAPs, and generating the priority indicator. In some examples, via the input unit 252 and the output unit 254, a system user may interactively annotate or mark on the presentation of the detected medical event, such as by adjudicating the detected arrhythmia episode (e.g., annotate with explanatory notes such as arrhythmia type, or label the arrhythmia episode as a true positive or false positive detection). Multiple detected medical events may be adjudicated in a descending order of the priority indicators of the arrhythmia episodes. The memory circuit 240 may be configured to update the database by integrating the detected medical event and the associated physiological data, optionally along with the annotations, adjudications, or other user feedback into the stored historical medical alerts.

The output unit 254 may include circuitry configured to adjust a priority of the detected medical event, and schedule a human-perceptible notification of the detected medical event using the adjusted priority. The adjustment of the priority may include reorganizing or sorting the detected medical events according to their event priority indicators. In an example, a plurality of medical events detected from a patient may each have their respective priority indicators. The output unit 254 may schedule a presentation of the plurality of medical events arranged in a specific order such as a descending order of the adjusted priorities. In some examples, the adjustment of priorities and the scheduling of the presentation may include reorganizing or sorting patients based on information about subject priority. For example, the medical events detected from a plurality of patients may be prioritized according to the subject priority, such that the PAPs may generally have lower priorities than the non-PAPs. The output unit 254 may schedule a presentation of the medical events associated with the non-PAPs before the presentation of the medical events associated with the PAPs. In some examples, medical events detected from a plurality of patients may be prioritized according to both the subject priority and the event priority. Within each patient (e.g., a PAP), the detected medical events that are more similar to the historical medical alerts of the same patient are assigned with lower event priorities than, and are presented to the healthcare provider after, the detected medical events that are less similar to the historical medical alerts.

The output unit 254 may include a display for displaying the patient physiological data associated with the detected medical event, intermediate measurements or computations such as the signal characteristics, similarity metrics, alert priority indicators, or one or more historical medical alerts that are deemed similar to the detected medical event according to the event analyzer circuit 232, among others. In some examples, the output unit 254 may display the detected medical events along with their respective priority indicators and PAP or non-PAP identifiers. The non-PAPs or the high-priority medical events may be color-coded, highlighted, or otherwise signified on the display to distinguish from the PAPs or the low-priority detected medical events. The output unit 254 may include a printer for printing hard copies of the detection information. The information may be presented in a table, a chart, a diagram, or any other types of textual, tabular, or graphical presentation formats. The presentation of the output information may include audio or other media format. In an example, the output unit 254 may generate alerts, alarms, emergency calls, or other forms of warnings to signal the system user about the detected medical events.

The optional therapy circuit 260 may be configured to deliver a therapy to the patient in response to the detection of the medical event. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 260 may modify an existing therapy, such as adjust a stimulation parameter or drug dosage.

Figure 3A:
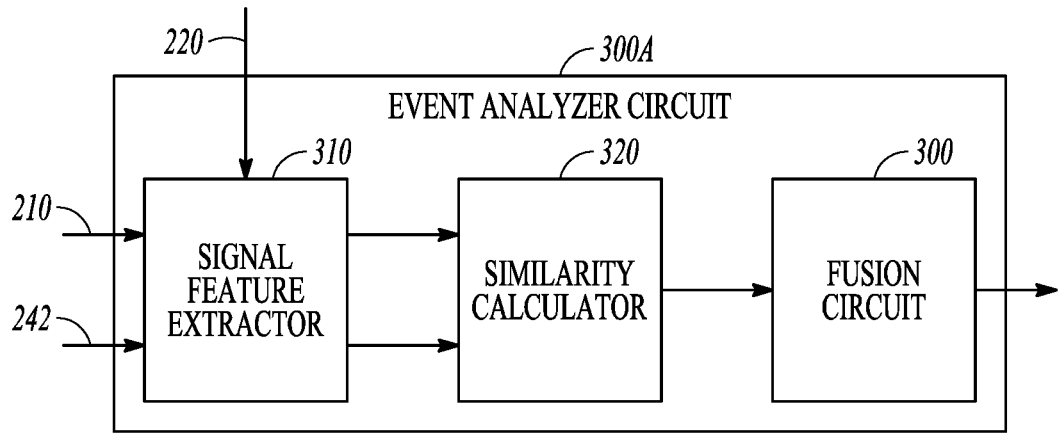
FIGS. 3A-B illustrates generally block diagrams of event analyzer circuits each configured to determine a similarity metric between a detected medical event to the historical medical alerts.
Figure 3B:
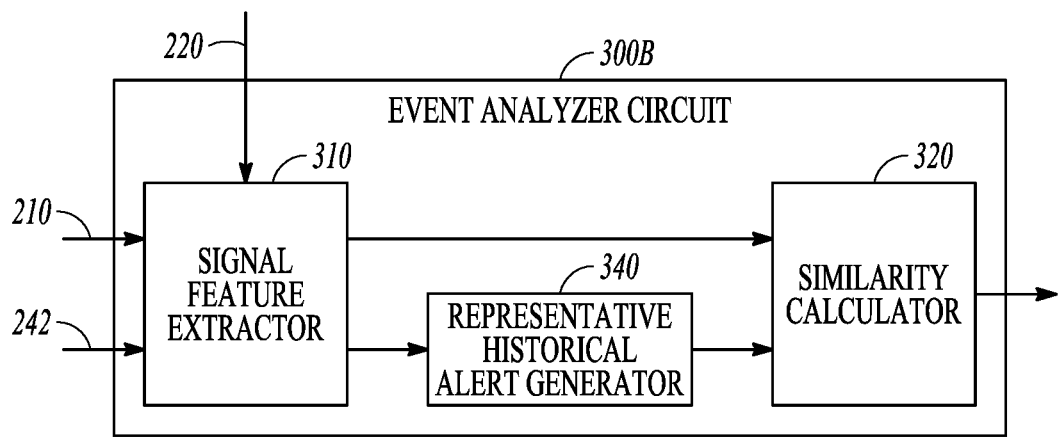

FIGS. 3A-B illustrates generally block diagrams of event analyzer circuits 300A and 300B each configured to determine a similarity metric between a detected medical event to the historical medical alerts 242. The event analyzer circuit 300A and 300B may each be an embodiment of the event analyzer circuit 232 of the alert management system 200.

As illustrated in FIG. 3A, the event analyzer circuit 300A may include a signal feature extractor 310, a similarity calculator 320, and a fusion circuit 330. The signal feature extractor 310 may extract signal characteristics from the physiological data Y sensed by the sensor circuit 210. The signal feature extractor 310 may additionally extract signal characteristics from the physiological data associated with the historical medical alerts 242, denoted by $\{X_1, X_2, \ldots, X_N\}$, where N indicates the number of historical alerts, and $X_i$ represents the stored information corresponding to the i-th historical alert.

The signal feature extractor 310 may use the extracted signal characteristics to construct a feature set, denoted by $Y=[Y(1), Y(2), \ldots, Y(M)]$, where M indicates the number of signal characteristics and $Y(j)$ represents measurement of the j-th signal characteristic. The signal characteristics may be generated from multiple data sources such as signals from multiple sensors. Alternatively or additionally, the signal characteristics may represent different statistical or morphological measurements from the same sensor signal. The signal feature extractor 310 may similarly extract from each $X_i$ (for i=1, 2, ..., N) a corresponding feature set, denoted by $X_i=[X_i(1), X_i(2), \ldots, X_i(M)]$, where $X_i(j)$ represents measurement of the j-th signal characteristic of the historical alert $X_i$. In an example, the physiological data Y and the stored historical physiological data $X_i$ may have different feature dimensions (e.g., Y includes M signal characteristics or features, and $X_i$ include K signal characteristics and K≠M), and Y and $X_i$ include at least one signal characteristic of the same type.

In an example, the detector circuit 220 detects a target medical event, such as a worsening heart failure (WHF) event, using multiple sensors including, for example, thoracic impedance sensor, heart sound sensor, respiration sensor, cardiac electrical activity sensor, or physical activity sensors, among others. The feature set for the detected medical event, $Y=[Y(1), Y(2), \ldots, Y(M)]$, includes signal characteristics extracted from different sensors, or from the same sensor. Similarly, the feature set for the i-th historical WHF event (among N historical alerts), $X_i=[X_i(1), X_i(2), \ldots, X_i(M)]$, may include signal characteristics corresponding to the M signal characteristics in Y. By way of example, if Y(j) represents a thoracic impedance (Z) trend measurement and Y(k) represents a third heart sound (S3) intensity trend measurement corresponding to the detected medical event, then $X_i(j)$ represents a Z trend measurement and $X_i(k)$ represents a S3 intensity trend measurement corresponding to the i-th historical WHF event.

The similarity calculator 320 may compute a similarity metric between the detected medical event and each of the historical medical alerts $\{X_1, X_2, \ldots, X_N\}$. The similarity metric can include a distance measure between the signal characteristics extracted from the physiological data associated with the detected medical event, and the signal characteristics extracted from the physiological data associated with the i-th alert, denoted by $d(Y, X_i)$. When both Y and $X_i$ are multi-dimensional feature sets where $Y=[Y(1), Y(2), \ldots, Y(M)]$ and $X_i=[X_i(1), X_i(2), \ldots, X_i(M)]$, the distance $d(Y, X_i)$ may be computed in the multi-dimensional feature space. Examples of the distance can include Euclidean distance, Mahalanobis distance, correlation coefficient, or a L1, L2, or infinite norm, among others.

In some examples, the similarity metric and the event prioritization may be further using the quality of the physiological data, such as a signal to noise ratio (SNR), of one or more physiological signals used for detecting the target medical event. In an example where the similarity metric is a Euclidean distance $d(Y, X_i)$ between Y and $X_i$, the squared differences of individual signal characteristics, such as $(Y(j)-X_i(j))^2$, may each be weighted by the respective SNRs associated with the signal characteristics, that is:

$$d(Y,X_i)=\sqrt{\sum_{j=1}^{M}\alpha_j \cdot (Y(j)-X_i(j))^2}, \text{ for } i=1,2,\ldots,N \quad (1)$$

where the weight factors $\{\alpha_j\}$ may be proportional to SNR of the physiological signal from which the signal characteristic Y(j) is extracted. A sensor signal with a higher SNR may be more dominant in determining the similarity metric than the sensor signal with a lower SNR. For example, the detector circuit 220 detects the target medical event using multiple sensors including a thoracic impedance signal and a heart sound signal. The physiological data $Y=[Y(1), Y(2), \ldots, Y(M)]$ corresponding to the detected medical event, represented by a multi-dimensional feature vector, includes the Y(j) representing a thoracic impedance trend measurement, and Y(k) representing a S3 intensity trend measurement. If the impedance signal has a higher SNR than the heart sound signal, then in computing the similarity metric between Y and $X_i$, a larger weight may be assigned to the impedance trend measurement than the S3 intensity trend measurement. In some examples, the weight factors $\{\alpha_j\}$ may be determined using the predictive power, or a historical performance, of a physiological signal or signal feature used for detecting the target medical event. In some other examples, the weight factors $\{\alpha_j\}$ may be user-programmable.

The fusion circuit 330 may use the resultant N similarity metrics, such as distance measures $\{d(Y, X_1), d(Y, X_2), \ldots, d(Y, X_N)\}$, to compute a composite similarity measure representing the similarity between the detected medical event and the stored historical alerts. The composite similarity measure may be computed as a weighted combination of the distance measures, that is:

$$D = \sum_{i=1}^{N} w_i * d(Y, X_i) \qquad (2)$$

In an example, the weight factors $\{w_i\}$ may be determined according to the temporal proximity of the historical medical alert to the detected medical event. A more recent historical alert such as $X_i$ (temporally proximal to the detected medical event) may correspond to a larger weight factor $w_i$ than a more remote historical alert such as $X_j$ (temporally distal to the detected medical event). In some examples, the composite similarity measure D may be computed using only a portion of historical medical alerts occurring during a specified period of time, such as within a week, a month, or a year prior to the detected medical event. The alert prioritizer circuit 234 may use the composite similarity measure D to prioritize the detected medical event.

FIG. 3B illustrates the event analyzer circuit 300B that may include a signal feature extractor 310, a similarity calculator 320, and a representative historical alert generator 340. The signal feature extractor 310 may extract signal characteristics Y from the physiological data associated with the detected medical event, and the signal characteristics $\{X_1, X_2, \ldots, X_N\}$ from the physiological data associated with N stored historical medical alerts. The representative historical alert generator 340, coupled to the signal feature extractor 310, may generate representative signal characteristics rX from the historical signal characteristics $\{X_1, X_2, \ldots, X_N\}$. In an example, rX may be computed as a central tendency of the signal characteristics of the N alerts $\{X_1, X_2, \ldots, X_N\}$. In another example, rX may be computed as a central tendency of the signal characteristics of a selected portion of the N alerts $\{X_1, X_2, \ldots, X_N\}$, such as those alerts occurring within a specified period of time prior to the detected medical event. Examples of the central tendency may include mean, median, mode, or measures taken from a statistical distribution of the stored physiological data $\{X_1, X_2, \ldots, X_N\}$. In an example, the representative historical signal characteristic rX is a centroid of the stored physiological data $\{X_1, X_2, \ldots, X_N\}$. The centroid measure represents signal characteristics of the most common historical medical alerts. When the historical medical alert $X_i$ is represented by a multi-dimensional feature set, the event analyzer circuit 232 may compute a centroid along each feature dimension across the historical alerts $\{X_1, X_2, \ldots, X_N\}$. The resultant representative historical signal characteristic rX may represent the centroid of $\{X_1, X_2, \ldots, X_N\}$ in a multi-dimensional feature space.

The similarity calculator 320 may compute a similarity metric between the signal characteristics of the physiological data Y and the representative historical signal characteristic rX, that is, $D = d(rX, Y)$. The alert prioritizer circuit 234 may use the composite similarity measure D to prioritize the detected medical event.

Figure 4:
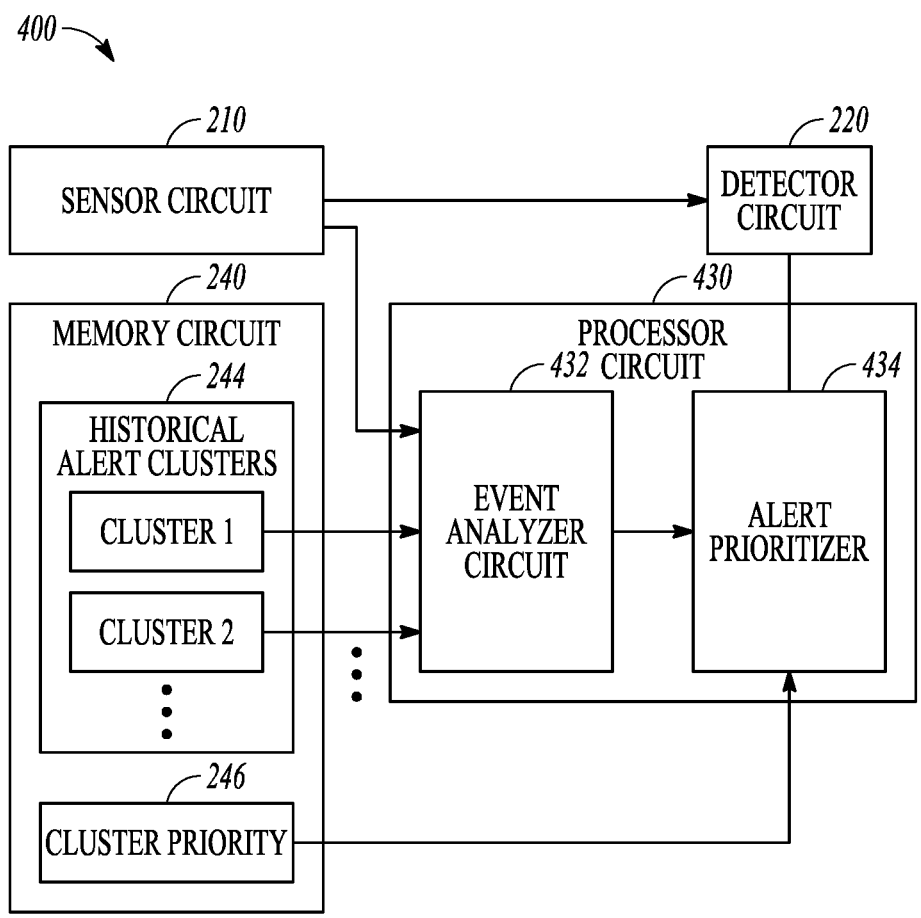
FIG. 4 illustrates generally a block diagram of an alert management system configured to prioritize a detection of a medical event using clusters of historical medical alerts.

FIG. 4 illustrates generally a block diagram of an alert management system 400 configured to prioritize a detection of a medical event using clusters of historical medical alerts. The alert management system 400, an embodiment of the alert management system 200, may include a processor circuit 430. The processor circuit 430 may include an event analyzer circuit 432 and an alert prioritizer 434. The event analyzer circuit 432, an embodiment of the event analyzer circuit 232, may receive from the sensor circuit 210 physiological data used for detecting the target medical event, and receive from the memory circuit 240 information about patient historical medical alerts.

The stored information about the historical medical alerts may include historical alert clusters 244 in the patient medical history. The alerts within the same cluster may have similar signal characteristics, such that a distance between the signal feature vectors associated with any two medical alerts within an alert cluster falls below a threshold value. For example, $X_i$ and $X_j$ belong to the same alert cluster if $d(X_i, X_j) < T$ where T denotes a threshold.

The historical medical alerts may be clustered into one or more alert clusters using unsupervised learning algorithms using the distance measure between alerts. In an example, the clustering algorithm may include a K-means clustering that minimizes an objective function such as total squared distance between the physiological data associated with individual alerts and the cluster center. The cluster center for each cluster represents a centroid of the alerts within the cluster. In another example, the clustering algorithm may include a fuzzy C-means clustering that minimizes an objective function such as total weighted squared distance between the physiological data associated with individual alerts and the cluster center, where the weight represents a degree of membership of a particular alert being within the cluster. Fuzzy partitioning of the medical alerts is carried out through an iterative optimization of the objective function with the update of membership and the cluster centers. Other examples of the clustering algorithm may include hierarchical clustering that uses iterative update of clusters by merging the alerts using the similarity metrics, or mixture of Gaussians or other model-based clustering algorithms, among others.

In addition to or in lieu of unsupervised clustering, the historical medical alerts may be clustered using a supervised learning algorithm, such as clustering according to user-specified criteria or cluster characteristics. In an example, alert clusters may be formed according to one, or a subset of, the signal characteristics, such as one or more value ranges of a physiological parameter. For example, alert clusters may include historical arrhythmia clusters defined by a heart rate range, such as clusters of 100-120 beats per minute (bpm), 120-150 bpm, 150-180 bpm, 180-220 bpm, etc. Historical arrhythmia clusters may be defined using ranges of other parameters, such as a heart rate stability range, signal amplitude or intensity range (such as intensities of a cardiac electrogram or a physiologic sensor measurement), atrioventricular timing range, an arrhythmia duration range, a physical activity intensity range or duration range, among others. The physiological parameter used for defining clusters may be specific to a particular arrhythmia type. For example, in detecting atrial tachyarrhythmia such as atrial fibrillation, the clusters may be defined as one or more of a heart rate variability range, a range of relative count (e.g., a ratio) of stable heart beats versus unstable heart beats within a specified time period, a range of heart rate density index (HRDI) representing a percentage of the heart beats falling within the histogram bin including the mode of the heart rates, a range of Wenkebach score indicative of frequency of abnormal atrioventricular conductions, or a range of cardiac morphology statistics, among others.

Clusters may be defined as one or more user specified event types. In an example, the historical medical alerts may be clustered according to one or more specified cardiac arrhythmia types, such as bradycardia, ventricular tachycardia, ventricular fibrillation, atrial tachycardia, atrial fibrillation, atrial flutter, supraventricular tachycardia, electric pauses, among others.

In some examples, at least some of the stored historical medical alerts may have been reviewed, assessed, or annotated by healthcare providers. For example, the historical medical alerts associated with arrhythmia episodes may be adjudicated as a specific arrhythmia type, or as one of a true positive (TP) detection, a false positive (FP) detection, a true negative (TN) detection, or a false negative (FN) detection. The stored historical medical alerts may be clustered according to the adjudication, such as a TP cluster, a FP cluster, a TN cluster, or a FN cluster.

Each cluster may have a cluster center with representative historical signal characteristic. The cluster center may be iteratively determined and updated during the clustering process. The cluster center may represent a centroid of the member alerts within the cluster, or a mean feature vector of a Gaussian or other statistical model of the cluster. By way of example and not limitation, the historical medical alerts may be clustered into K clusters with the cluster centers denoted by $\{C_1, C_2, \ldots, C_K\}$. Each cluster center may be represented by a multi-dimensional feature vector, such as $C_i=[C_i(1), C_i(2), \ldots, C_i(M)]$, where M indicates a total number of signal characteristics. The event analyzer circuit 432 may compute similarity metrics between the feature vector $Y=[Y(1), Y(2), \ldots Y(M)]$ associated with the detected medical event, and each of the cluster centers $C_i$ for $i=1, 2, \ldots, K$. The similarity metric may be computed as a distance measure, denoted by $d(Y, C_i)$ in a multi-dimensional feature space.

The alert prioritizer 434, which may be an embodiment of the alert prioritizer 234, may generate an event priority indicator for the detected medical event using the similarity metrics $\{d(Y, C_1), d(Y, C_2), \ldots, d(Y, C_K)\}$. In an example, the alert prioritizer 434 may be coupled to the memory circuit 240 to receive a cluster priority 246. The cluster priority 246 may be a predetermined or user-specified quantity indicating relative significance of one cluster over another. The alert prioritizer 434 may generate an event priority indicator for the detected medical event further using the cluster priority 246. For example, if $C_1$ is the center of cluster #1 and $C_2$ is the center of cluster #2, and the cluster priority 246 provides that cluster #1 has a higher cluster priority than cluster #2, then a higher priority is assigned to Y if $d(Y, C_1)<d(Y, C_2)$, because Y is similar to the historical alerts with higher designated priority (i.e., cluster #1).

In an example, the historical medical alerts are clustered as one of a TP cluster (with a cluster center $C_{TP}$) and FP cluster (with a cluster center $C_{FP}$), a higher priority may be assigned to the TP cluster than to the FP cluster, at least because the TP cluster represents alerts associated with true occurrence of the target medical events such as an arrhythmia or WHF, while the FP cluster represents false alerts associated with non-occurrence of the target medical events. The alert prioritizer 434 may assign a higher priority to the detected medical event Y if the detected medical event Y is more similar to the TP cluster that to the FP cluster (e.g., $d(Y,C_{TP})$ being shorter than $d(Y, C_{FP})$ by a specific margin), or assign a lower priority to Y if the detected medical event Y is more similar to the FP cluster (e.g., $d(Y,C_{RP})$ being greater than $d(Y, C_{FP})$ by a specific margin). This may ensure a detected medical event that is more likely a true arrhythmia episode to receive immediate review by the healthcare provider than other detected medical events that are more likely a FP detection.

The detected medical event, once reviewed and adjudicated by the healthcare provider, may be integrated into the database in the memory circuit 240, and become a part of the historical medical alerts. Adjudication, annotation, or other user-provided feedback may also be associated with the detected medical event and integrated into the database. In an example, using the adjudication, the detected medical event may be classified into one of existing clusters, such as a TP or FP cluster, a specific medical event type cluster (e.g., a specific cardiac arrhythmia cluster), or a signal characteristic value range cluster. Alternatively, a new cluster may be formed if the detected medical event is dissimilar to any of the existing clusters, such as when a distance measure between the multi-dimensional feature set of the detected medical event and each cluster center of the existing clusters exceeds a threshold value.

Figure 5:
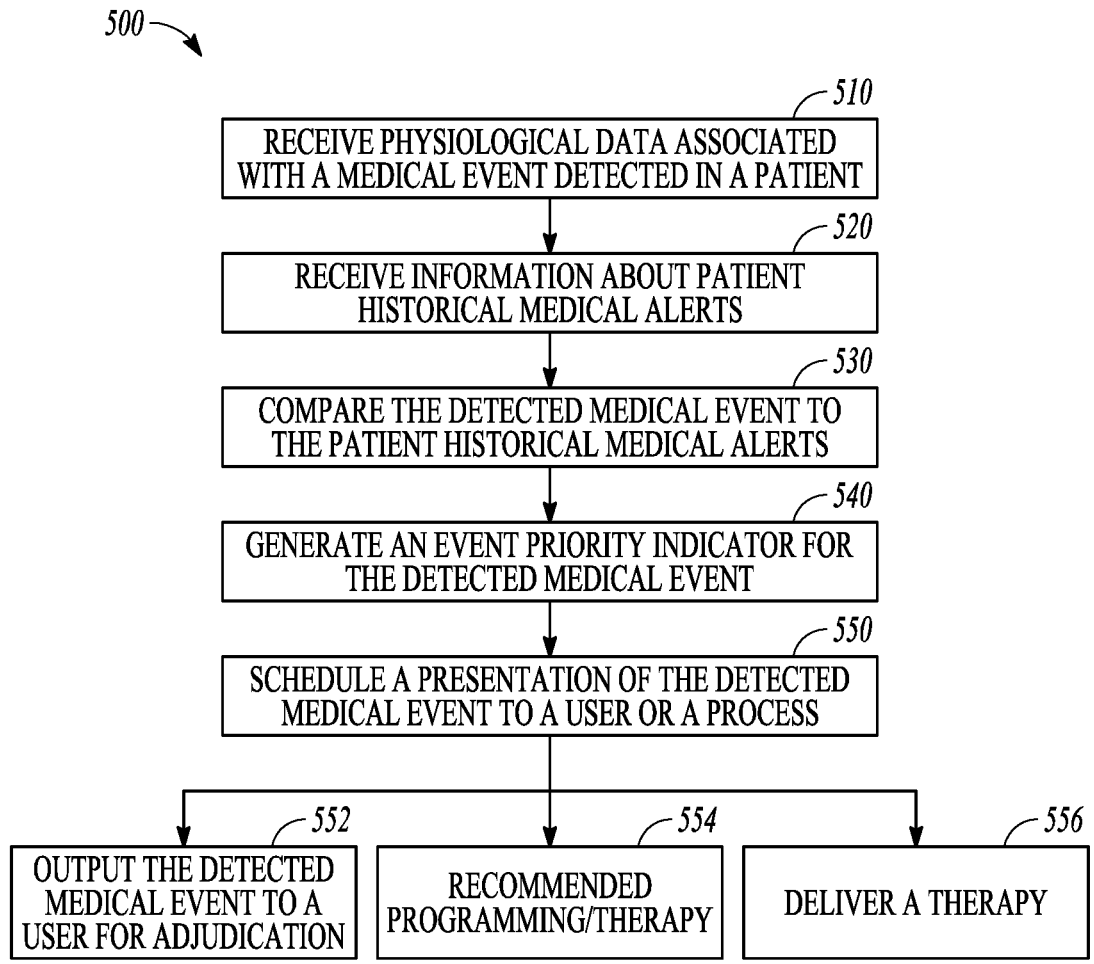
FIG. 5 illustrates generally an example of a method for managing machine-generated medical alerts.

FIG. 5 illustrates generally an example of a method 500 for managing machine-generated medical alerts. The method 500 may be implemented and executed in an ambulatory medical device such as an implantable or wearable medical device, or in a remote patient management system. In an example, the method 500 may be implemented in and executed by the AMD 110, one or more devices in the external system 125, or the alert management systems 200 or 400.

The method 500 begins at 510, where physiological data associated with a medical event detected in a patient may be received. The physiological data may include one or more physiological signals such as sensed by the sensor circuit 210. Examples of the physiological signals may include a cardiac electrical signal, such as an electrocardiography (ECG) or an intracardiac electrogram (EGM), thoracic or cardiac impedance signal, arterial pressure signal, pulmonary artery pressure signal, left atrial pressure signal, RV pressure signal, LV coronary pressure signal, heart sounds or endocardial acceleration signal, physiological response to activity, apnea hypopnea index, one or more respiration signals such as a respiration rate signal or a tidal volume signal, among others. The sensed physiological signal may be pre-processed, including one or more of signal amplification, digitization, filtering, or other signal conditioning operations. In some examples, signal metrics such as timing parameters, or statistical or morphological parameters may be detected from the sensed physiological signal. The physiological data received at 510 may additionally include contextual data such as time of day, temperature, environmental parameters, or patient medical record information.

The physiological data received at 510 may be associated with a medical event such as a cardiac arrhythmia episode, worsening of a chronic medical condition such as worsening heart failure (WHF). The medical event may be detected from one or more physiological signals such as by using the detector circuit 220. The detected medical events may additionally or alternatively include patient-triggered events, such as when the patient experiences a target medical event.

At 520, information about patient historical medical alerts may be received. Such information may include a database of physiological data associated with the medical alerts in the patient medical history. The stored physiological data may be of the same types as the physiological data associated with the target medical event. For example, if the medical event is an arrhythmia episode detected from cardiac electrograms sensed from a specific sensing vector comprising an anode and a cathode, the physiological data associated with the historical medical alerts may include the cardiac electrograms sensed according to the same sensing vector.

At 530, the detected medical event may be compared to the patient historical medical alerts. A similarity metric may be computed between the physiological data associated with the detected medical event and the stored physiological data associated with the historical medical alerts. The similarity metric may include a distance measure such as Euclidean distance, Mahalanobis distance, correlation coefficient, or a L1, L2, or infinite norm, among others.

In an example, signal characteristics may be extracted from the physiological data associated with the detected medical event. The detected medical event may thus be represented by a multi-dimensional feature vector $Y=[Y(1), Y(2), \ldots, Y(M)]$. Similarly, signal characteristics may be extracted from the physiological data associated with a historical medical alert. For example, of N historical medical alerts denoted by $\{X_1, X_2, \ldots, X_N\}$, where $X_i$ represents the stored information corresponding to the i-th historical alert, each historical medical alert may be represented by a corresponding multi-dimensional feature vector, such as $X_i=[X_i(1), X_i(2), \ldots, X_i(M)]$. A similarity metric between the feature vector associated with the detected medical event, and the feature vector of each of the historical medical alert, may be computed. In an example, the similarity metric may include a distance $d(Y, X_i)$ in the multi-dimensional feature space. A composite similarity measure may then be computed using the resultant similarity metrics, such as N distance measures $\{d(Y, X_1), d(Y, X_2), \ldots, d(Y, X_N)\}$. The composite similarity measure may be computed using the event analyzer circuit 300A. In an example, the composite similarity measure may be computed as a weighted combination of the distance measures $\{d(Y, X_1), d(Y, X_2), \ldots, d(Y, X_N)\}$. The weight factors may be determined according to the temporal proximity to the detected medical event, as previously discussed with reference to FIG. 3A.

At 540, an event priority indicator may be generated for the detected medical event. The similarity metric may be compared to one or more threshold values, or ranges of values, and the detected medical event may be categorized as one of a plurality of predetermined degrees of priority, such as a high priority, medium priority, or low priority. The degree of priority may be inversely related to the similarity metric, such that a lower priority may be assigned to a detected medical event that is similar to the historical alerts, and a higher priority may be assigned to a detected medical event that is dissimilar to the historical alerts. The detected medical events that are dissimilar to the historical alerts may indicate new medical conditions not seen in patient medical history, or a variation or progression of a historical medical event. Such medical events may require immediate attention by a healthcare provider.

In some examples, the information about the historical medical alerts received at 520 may include indicators of severity or clinical significance of the medical events associated with the historical medical alerts. The severity indicators may be provided by a clinician. In an example, historical medical events that result in physician intervention or hospitalization may be designated as severe historical medical alerts. The detected medical event may be compared to the severe historical medical alerts and to other non-severe historical medical alerts at 530 to compute a similarity metric between the detected medical event and the historical severe medical alerts, and a similarity metric between the detected medical event and the historical non-severe medical alerts. At 540, a higher priority may be assigned to the detected medical event if it is similar to the severe historical medical alert, or if it is dissimilar to the severe or non-severe historical alerts. A lower priority may be assigned if the detected medical event is similar to the non-severe historical alerts. The medical events with characteristics similar to severe medical events in patient medical history are likely of clinical significance. A higher priority assigned to such events may ensure immediate medical attention and intervention as needed. In some examples, at 540, a highest priority may be assigned to the detected medical event that is similar to the severe historical alert, followed by the detected medical event dissimilar to the severe or non-severe historical alerts, and a lowest priority may be assigned to the detected medical event that is similar to the non-severe historical alerts.

At 550, the detected medical event may be scheduled for being presented to a user or a process, such as via the output unit 254 of the alert management system 200. A priority of the detected medical event, such as for presentation to a user or a process, may be adjusted using the event priority indicator. In an example, a plurality of medical events detected from a patient may each have their respective priority indicators. Scheduling of the presentation may include timing of presenting the medical event, or an order of presenting the plurality of medical events, using their respective event priorities. In an example, the medical events detected from a particular patient may be sorted in a descending order of the event priority indicators.

The prioritized medical event may then be used in one or more of the processes 552, 554, or 556. At 552, the detected medical event may be output to a user, such as via the output unit 254 as illustrated in FIG. 2. Information may be displayed on a display, including the patient physiological data associated with the detected medical event, intermediate measurements or computations such as the signal characteristics, similarity metrics, alert priority indicators, or one or more historical medical alerts that are deemed similar to the detected medical event, among others. Additionally or alternatively, a hard copy of the detection information may be generated. A system user, such as a healthcare provider, may interactively annotate, mark on, or comment on the detected medical event, such as via the input unit 252. In an example, a system user may adjudicate the detected arrhythmia episodes in an order according to the priority indicators of the arrhythmia episodes. The detected medical event and the associated physiological data, optionally along with the annotations, adjudications, or other user feedback may be integrated into the database of the historical medical alerts.

At 554, a recommendation may be generate and provided to the user. The recommendation may include one or more of further diagnostic tests to be performed or therapies to administer. The recommendation may also include system-programming recommendations, such as adjustment of one or more parameters, such as detection parameters that may be used to improve sensitivity or specificity of detecting a target medical event.

The method 500 may include the optional step 556 of delivering a therapy to the patient in response to the detection of the medical event, such as via the optional therapy circuit 260 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy may be modified such as by adjusting a stimulation parameter or drug dosage.

Figure 6:
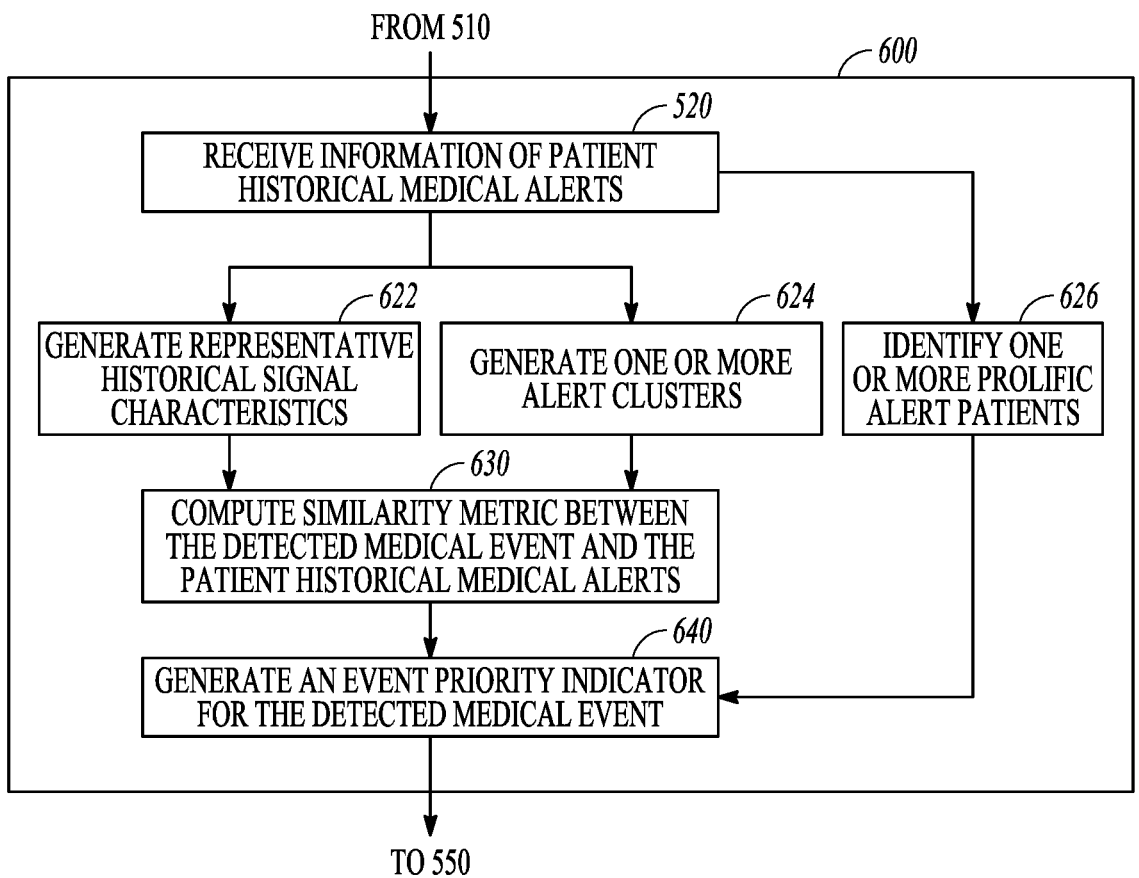
FIG. 6 illustrates generally an example of a method for prioritizing a device-detected medical event for presenting to a user or a process.

FIG. 6 illustrates generally an example of a method 600 for prioritizing a device-detected medical event for presenting to a user or a process. The method 600 may be an embodiment of at least a portion of the method 500, including some or all of steps 520 through 540. In an example, the method 600 may be implemented in and executed by the alert management system 200 in FIG. 2 or the alert management system 400 in FIG. 4.

The method 600 includes a step of receiving information of patient historical medical alerts at 520. Such information may include a database of physiological data associated with the medical alerts in the patient medical history, as discussed with reference to the method 500. The patient historical medical alerts may be processed in one or more ways to produce statistics for use in prioritizing the detected medical event. At 622, representative historical signal characteristics rX may be generated from a plurality of historical signal characteristics $\{X_1, X_2, \ldots, X_N\}$ corresponding to N historical medical alerts, such as by using the event analyzer circuit 300B. The representative historical signal characteristic rX may be computed as a central tendency of the signal characteristics of the stored physiological data $\{X_1, X_2, \ldots, X_N\}$. The rX may alternatively be computed as a central tendency of the signal characteristics of a selected portion of $\{X_1, X_2, \ldots, X_N\}$, such as those corresponding to the alerts during a specified period of time. In an example, the rX is a centroid of the stored physiological data $\{X_1, X_2, \ldots, X_N\}$, representing signal characteristics of the most common historical medical alerts.

The information of patient historical medical alerts may additionally or alternatively be processed at 624, where one or more alert clusters may be formed. The historical medical alerts, or a subset of the historical medical alerts, may be clustered into one or more alert clusters using unsupervised learning algorithms using the distance measure between alerts. Examples of the unsupervised clustering algorithms may include K-means, fuzzy C-means, hierarchical clustering, or model-based clustering such as mixture of Gaussians, among others. The historical medical alerts, or a subset thereof, may additionally or alternatively be clustered using a supervised learning algorithm, such as according to user specified criteria or cluster characteristics. In an example, clusters may be formed according to a signal characteristic, such as one or more value ranges of a physiological parameter. In another example, clusters may be defined as one or more user specified event types, such as one or more specified cardiac arrhythmia types. In yet another example, at least some of the stored historical medical alerts may have been reviewed, assessed, or annotated by healthcare professionals. The stored historical medical alerts may be clustered according to the adjudication, such as a true positive (TP) cluster or a false positive (FP) cluster, among others.

Each cluster may have a cluster center with representative historical signal characteristic. Each cluster center may be represented by a multi-dimensional feature vector. The cluster center may be iteratively updated and determined in the clustering process. The cluster center may represent a centroid of the member alerts within the cluster, or a mean feature vector of a Gaussian or other statistical model of the cluster.

At 630, a similarity metric between the detected medical event and the patient historical medical alerts may be computed. In an example, the similarity metric may be computed as a distance in a multi-dimensional feature space, between the signal characteristics Y associated with the detected medical event and the representative historical signal characteristic rX generated at 622, that is, D=d(rX, Y). The similarity may alternatively be computed between the detected medical event and one or more alert clusters. In an example, a distance between the signal characteristics Y associated with the detected medical event and each of the K cluster centers $C_i=[C_i(1), C_i(2), \ldots, C_i(M)]$, for i=1, 2, ..., K, may be computed, resulting in K similarity metrics $\{d(Y, C_1), d(Y, C_2), \ldots, d(Y, C_K)\}$ corresponding to K clusters. The distance $d(Y, C_i)$ may be computed as Euclidean distance, Mahalanobis distance, correlation coefficient, or a L1, L2, or infinite norm, in a multi-dimensional feature space.

At 640, an event priority indicator for the detected medical event may be generated. In an example, the composite similarity measure D may be compared to one or more threshold values or ranges of values, and categorized into one of a plurality of priority levels. In another example, the detected medical event is prioritized using the K similarity metrics $\{d(Y, C_1), d(Y, C_2), \ldots, d(Y, C_K)\}$ and a cluster priority. The cluster priority may be a predetermined or user-specified quantity indicating relative significance of one cluster over another. For example, a higher priority may be assigned to a true positive (TP) cluster the comprises adjudicated historical alerts representing true event detections, and a lower priority may be assigned to a false positive (FP) cluster that comprises adjudicated historical alerts representing false event detections. If the detected medical event is similar to the TP cluster, then a high priority may be designated. Otherwise, a low priority is designated if the detected medical event is more similar to the FP cluster. The prioritized medial event may then be scheduled for being presented to a user or a process at 550.

The detected medical event, once reviewed and adjudicated by the healthcare provider, may be integrated into the alert database such as stored and maintained in the memory circuit 240, and become a part of the historical medical alerts. The updated medical alerts in the database (with the inclusion of the detected medical event) may be re-clustered to form a new set of alert clusters each comprising updated alert members. In an example where multiple alert clusters are maintained in the database, the detected medical event may be assigned to one of the existing alert clusters, such as a TP or FP cluster, a specific medical event type cluster (e.g., a specific cardiac arrhythmia cluster), or a signal characteristic value range cluster. Alternatively, a new cluster may be formed if the detected medical event is dissimilar to any of the existing clusters.

The information of patient historical medical alerts received at 520 may additionally be used to identify one or more prolific alert patients at 626, such as by using the patient identifier circuit 236. A PAP is one having a large quantity of medical alerts of the same type (e.g., alerts of atrial fibrillation episodes) within a short time period. A majority of the alert notifications may come from a small percentage of the PAPs. Frequent alerts from a PAP may likely be repeating alerts that correspond to medical events of substantially similar characteristics, repeating false positive detections, or frequent patient-triggered events. As such, in prioritizing the alerts such as for evaluation and adjudication by a healthcare provider, the large volume of alerts from a PAP may be of less significance than the alert from a non-PAP. A PAP may be identified at 626 if the total count of historical medical alerts associated with the patient exceeds a threshold, or if the frequency of historical medical alerts with a specific period of time exceeds a threshold value.

The identification of the PAP may be used at 640 in prioritizing the medical events. In an example, the medical events detected from multiple patients may be prioritized through a process including a subject prioritization and an event prioritization. The subject prioritization may be using the identification of a PAP, who is designated with a lower subject priority than a non-PAP. Within each patient, the event prioritization may be using the similarity metric between the detected medical event and the historical medical alerts of the same patient. A lower event priority is assigned to the detected medical event that is more similar to the historical medical alerts, and a higher event priority is assigned if the detected medical event is not similar to the historical medical alerts. The scheduling of the presentation of the detected medical event at 550 may determine the timing or an order of presenting detected medical events from multiple patients to a system user or a process, according to both the subject prioritization and the event prioritization. In an example, the PAPs are presented after the non-PAPs, and the high-priority events are presented before the low-priority events within each patient.

Figure 7:
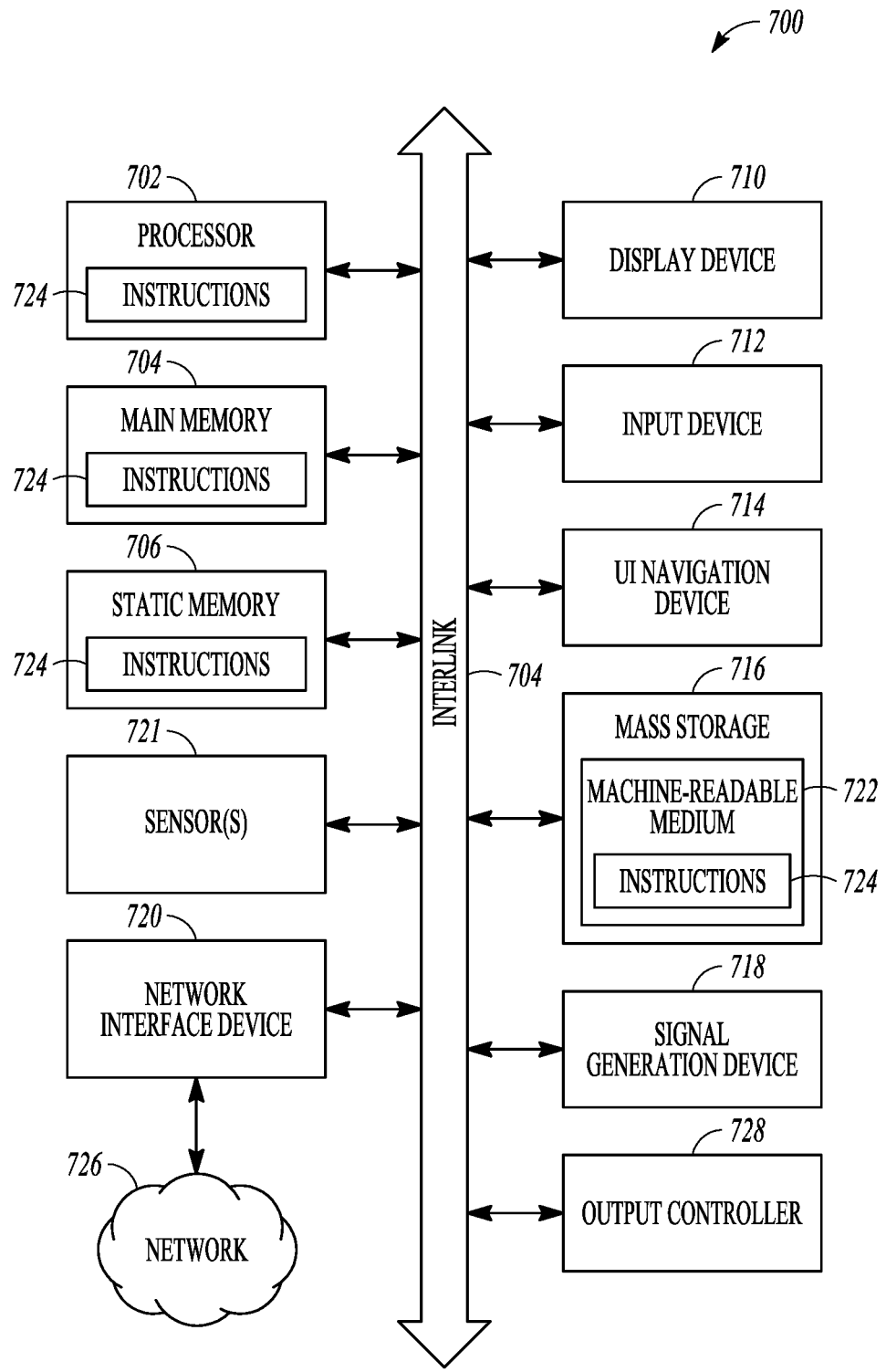
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the AMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one or more of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for managing machine-generated medical alerts, the system comprising:
    a receiver circuit configured to receive a medical event detected from a patient and information of historical medical alerts associated with the patient;
    an alert prioritizer circuit configured to generate an event priority indicator for the detected medical event using the detected medical event and the information of historical medical alerts;
    a patient identifier circuit configured to identify a prolific alert patient, the prolific alert patient having a quantity of historical medical alerts exceeding a threshold quantity value during a specified time period; and
    an output circuit configured to adjust an alert timing or an alert order based on the generated event priority indicator, and to schedule a presentation of the detected medical event using the identification of the prolific alert patient.

2. The system of claim 1, wherein the alert prioritizer circuit is configured to adjust a priority of the detected medical event by lowering the priority of the detected medical event when the detected medical event is similar to events in the information of historical medical alerts.

3. The system of claim 1, wherein the alert prioritizer circuit is configured to adjust a priority of the detected medical event by increasing the priority of the detected medical event when the detected medical event is dissimilar to events in the information of historical medical alerts.

4. The system of claim 1, wherein the information of the historical medical alerts includes existing alerts stored in a memory.

5. The system of claim 1, further comprising:
    a sensor circuit configured to sense a physiological signal from the patient; and
    a detector circuit configured to detect the detected medical event using the sensed physiological signal;
    wherein the alert prioritizer circuit is configured to generate the event priority indicator using a comparison between the detected medical event and the information of historical medical alerts.

6. The system of claim 5, wherein the information of historical medical alerts includes a plurality of historical physiological signal characteristics corresponding to the historical medical alerts, and the alert prioritizer circuit is configured to:
    extract a signal characteristic from the sensed physiological signal in response to the detection of the medical event;
    compute a similarity metric between (1) the extracted signal characteristic corresponding to the detected medical event and (2) the plurality of the historical physiological signal characteristics corresponding to the historical medical alerts; and
    generate the event priority indicator inversely related to the similarity metric.

7. The system of claim 6, wherein the alert prioritizer circuit is configured to:
    generate a representative historical signal characteristic from the plurality of historical physiological signal characteristics corresponding to the historical medical alerts; and
    compute a similarity metric between (1) the extracted signal characteristic corresponding to the detected medical event and (2) the representative historical signal characteristic.

8. The system of claim 1, wherein:
    the alert prioritizer circuit is configured to generate, for a plurality of detected medical events, respective event priority indicators; and
    the alert prioritizer circuit is configured to adjust priorities of the plurality of detected medical events using the respective event priority indicators, and to schedule a human-perceptible presentation of the plurality of medical events arranged in a descending order of the adjusted priorities.

9. The system of claim 1, wherein the medical event includes a cardiac event.

10. The system of claim 1, wherein the output circuit is configured to generate an alert of the detected medical event only if the event priority indicator satisfies a condition.

11. The system of claim 1, wherein the output circuit is configured to generate an alert of the medical event detected from the identified prolific alert patient based on the quantity of historical medical alerts of the identified prolific alert patient during the specified time period.

12. A method for managing machine-generated medical alerts via a medical system, the method comprising:
receiving a medical event detected from a patient and information of historical medical alerts associated with the patient using a receiver circuit;
generating, using an alert prioritizer circuit, an event priority indicator for the detected medical event using the detected medical event and the information of historical medical alerts;
identifying a prolific alert patient having a quantity of historical medical alerts exceeding a threshold quantity value during a specified time period; and
using an output circuit, adjusting an alert timing or an alert order based on the event priority indicator, and scheduling a presentation of the detected medical event using the identification of the prolific alert patient.

13. The method of claim 12, further comprising adjusting a priority of the detected medical event, wherein the adjusting the priority of the detected medical event includes one or more of:
lowering the priority of the detected medical event when the detected medical event is similar to events in the information of historical medical alerts; or
increasing the priority of the detected medical event when the detected medical event is dissimilar to events in the information of historical medical alerts.

14. The method of claim 12, wherein the information of historical medical alerts includes a plurality of historical physiological signal characteristics corresponding to the historical medical alerts, the method further comprising:
receiving a physiological signal from the patient during the detected medical event;
extracting a signal characteristic from the received physiological signal;
computing a similarity metric between (1) the extracted signal characteristic corresponding to the detected medical event and (2) the plurality of the historical physiological signal characteristics corresponding to the historical medical alerts; and
generating the event priority indicator inversely related to the similarity metric.

15. The method of claim 14, further comprising generating a representative historical signal characteristic from the plurality of historical physiological signal characteristics corresponding to the historical medical alerts;
wherein computing the similarity metric includes computing a distance between (1) the extracted signal characteristic corresponding to the detected medical event and (2) the representative historical signal characteristic.

16. The method of claim 14, wherein the historical medical alerts includes one or more alert clusters each comprising one or more historical physiological signal characteristics, and wherein:
computing one or more similarity metrics respectively for the one or more alert clusters, the one or more similarity metrics each being computed between (1) the extracted signal characteristic corresponding to the detected medical event and (2) the one or more historical physiological signal characteristics of the corresponding alert cluster; and
generating the event priority indicator using the one or more similarity metrics and a cluster priority.

17. A system for managing machine-generated medical alerts, the system comprising:
a sensor circuit configured to sense a physiological signal from a patient; and
a detector circuit configured to detect a medical event using the sensed physiological signal;
a receiver circuit configured to receive information of historical medical alerts associated with the patient, the information of historical medical alerts including one or more alert clusters each comprising one or more historical physiological signal characteristics;
an alert prioritizer circuit configured to:
extract a signal characteristic from the sensed physiological signal in response to the detection of the medical event;
compute one or more similarity metrics respectively for the one or more alert clusters, the one or more similarity metrics each being computed between (1) the extracted signal characteristic corresponding to the detected medical event and (2) the one or more historical physiological signal characteristics of the corresponding alert cluster; and
generate an event priority indicator using the one or more similarity metrics and a cluster priority, the event priority indicator inversely related to at least one of the one or more similarity metrics; and
an output circuit configured to adjust an alert timing or an alert order based on the generated event priority indicator.

18. The system of claim 17, wherein the one or more alert clusters include at least one of:
a true positive alert cluster comprising historical physiological signal characteristics corresponding to true positive detections of historical medical events;
or a false positive alert cluster comprising historical physiological signal characteristics corresponding to false positive detections of historical medical events.

19. The system of claim 17, wherein the one or more alert clusters include one or more medical event types.

20. The system of claim 17, wherein the one or more alert clusters include one or more value ranges of a physiological parameter.

* * * * *